United States Patent
Kusuzono et al.

(10) Patent No.: US 6,536,643 B2
(45) Date of Patent: Mar. 25, 2003

(54) METHOD FOR DETECTING BREAK POINT OF THREAD AND APPARATUS THEREFOR

(75) Inventors: Hiroaki Kusuzono, Matsuyama (JP); Bunji Hamasu, Matsuyama (JP); Mitsumasa Sasaki, Matsuyama (JP); Shunzo Naito, Matsuyama (JP)

(73) Assignees: Teijin Limited, Osaka (JP); Teijin Seiki Textile Machinery Co., Ltd., Ehime (JP)

( * ) Notice: Subject to any disclaimer, the term of this patent is extended or adjusted under 35 U.S.C. 154(b) by 0 days.

(21) Appl. No.: 09/936,292
(22) PCT Filed: Jan. 25, 2001
(86) PCT No.: PCT/JP01/00498
  § 371 (c)(1),
  (2), (4) Date: Sep. 12, 2001
(87) PCT Pub. No.: WO01/55022
  PCT Pub. Date: Aug. 2, 2001

(65) Prior Publication Data
US 2002/0157223 A1 Oct. 31, 2002

(30) Foreign Application Priority Data
Jan. 28, 2000 (JP) ......................................... 2000-020098

(51) Int. Cl.⁷ .......................... B65H 43/00; G01L 5/04
(52) U.S. Cl. .......................... 226/11; 57/265; 73/160; 226/100; 242/485.2
(58) Field of Search ........................... 226/10, 11, 100; 242/485.2; 57/265; 73/1.79, 160; 340/677

(56) References Cited

U.S. PATENT DOCUMENTS

| | | | | |
|---|---|---|---|---|
| 3,759,026 A | * | 9/1973 | Hope | 226/11 |
| 3,863,241 A | * | 1/1975 | Kamiyamaguchi et al. | 226/11 |
| 4,067,554 A | * | 1/1978 | Koch | 366/84 |
| 4,477,398 A | | 10/1984 | Henry et al. | |
| 5,682,146 A | * | 10/1997 | Neumann | 57/264 |
| 5,844,494 A | * | 12/1998 | Spahlinger et al. | 57/265 |
| 5,862,660 A | * | 1/1999 | Haasen et al. | 57/264 |
| 6,123,283 A | * | 9/2000 | Hayashi et al. | 242/485.2 |

FOREIGN PATENT DOCUMENTS

| | | |
|---|---|---|
| JP | 10-151289 | 6/1998 |
| JP | 11-139690 | 5/1999 |

* cited by examiner

Primary Examiner—Michael R. Mansen
(74) Attorney, Agent, or Firm—Rader, Fishman & Grauer PLLC

(57) ABSTRACT

A yarn breakage position detecting device and method of detecting a yarn breakage position involves a running yarn tension detector arranged at a reference position and that outputs a tension signal by which occurrence of yarn breakage is detected, and passage of the end of a broken yarn through the reference position is then calculated based on the time period from occurrence of yarn breakage to passage of the broken yarn end through the reference position. The yarn breakage time is stored as a time at which the tension signal becomes a peak value and/or a time at which the tension signal begins to decrease below a steady state tension value. The time when the yarn passes through the reference position is stored as a time at which the tension signal becomes lower than a lower limit value and/or a time at which natural oscillation begins.

15 Claims, 4 Drawing Sheets

METHOD FOR DETECTING BREAK POINT OF THREAD AND APPARATUS THEREFOR

TECHNICAL FIELD

The invention relates to a yarn breakage position detecting method and a device which can detect a yarn breakage occurrence position when a running yarn is broken in a variety of textile machines and textile manufacturing processes.

BACKGROUND ART

In the manufacturing process of a synthetic textile, more specifically, in the manufacturing process of a finished yarn of filaments, there are a spinning stage, a drawing stage, a false twisting stage and other process stages, as is well known. In each of these stages, a variety of processing units, such as guides, rollers, a heater and a false-twisting disc are placed over the entire length of each stage, for example, over an 8 to 10 m long stage, and continuous production is carried out while a yarn is running therethrough. In these stages, breakage of a yarn is usually managed, by a yarn breakage managing device having a yarn breakage detector placed just before the winding portion of each spindle for detecting a yarn breakage, so that the yarn breakage managing device automatically carries out appropriate actions, such as stopping the yarn feeding by the spindle at which a yarn breakage occurs. This prevents troubles, such as a swelling of a roller caused by a broken yarn wound onto the roller, which may induce another yarn breakage in an adjacent spindle.

As mentioned above, however, these stages have many processing members, such as guides, rollers, a heater and a false twisting disc and so on, and each of the processing members may be a cause of an occurrence of yarn breakage. In the case where a yarn breakage frequently occurs due to these processing members, the above mentioned yarn breakage managing device can play its roll if it is only necessary to identify a specific spindle suffering from a frequent yarn breakage within all the spindles. However, a yarn breakage occurs due to many causes, and in the case where the cause of the yarn breakage is to be investigated, a problem arises that there are too many possible causes to promptly analyze them. Therefore, even if countermeasures are taken for respective causes one by one, the yarn breakage problems may not be solved, and lowered productivity is inevitable because this may result in many commercially improper packages due to insufficiency of wound yarn and, in the end, the spindle may be kept stopped until the next periodic maintenance of equipment. With the intensifying demand for cost reduction these days, a solution to this situation is now earnestly sought.

SUMMARY OF THE INVENTION

An object of the present invention, in view of the above mentioned situation, is to establish a method and means for clarifying causes of a yarn breakage when the yarn breakage occurs and, thereby, provide a yarn breakage position detecting method and a device capable of immediately clarifying in which stage the yarn breakage occurs.

According to the present invention, there is provided a method of detecting a yarn breakage position where a running yarn is broken in a yarn processing equipment, which comprises the steps of detecting occurrence of yarn breakage by monitoring tension of the running yarn, detecting passage of an end of the broken yarn through a reference position, detecting a period of time from occurrence of the yarn breakage to passage of the yarn end through the reference position, and calculating the yarn breakage position relative to the reference position based on said period of time.

Also, according to the present invention, there is provided a device of detecting a yarn breakage position where a running yarn is broken in a yarn processing equipment, which comprises a tension detector arranged at a reference position and in contact with a running yarn to detect tension of the running yarn, a yarn breakage occurrence detecting means detecting a first time when the yarn is broken by using a tension signal of said tension detector, a yarn end passage detecting means detecting a second time when the broken yarn end passes through the reference position, and a position detecting means detecting the yarn breakage position relative to the reference position based on said first time and said second time.

As is apparent from the above mentioned configuration, in the present invention, the time of occurrence of a yarn breakage is detected and then the time of passage of the broken yarn end is detected at a predetermined reference position. In addition, there is the feature that the position of the yarn breakage relative to the reference position is determined based on the difference between the detected time of occurrence of the yarn breakage and the detected time of passage of the yarn end formed due to the breakage.

Therefore, the yarn breakage position detecting method and the device of the present invention can detect not only whether a yarn breakage occurs, as in the prior art, but also a position where a yarn breakage occurs, which the prior art cannot provide. Therefore, it is possible to immediately identify which processing members cause a yarn breakage in a production stage as mentioned earlier. This means that it is possible to quickly find and fix a specific position or processing member or portion that may frequently cause yarn breakage unless fixed. Therefore, the problem of lowered productivity, mentioned earlier, can be overcome.

Further, because both the occurrence of a yarn breakage and the passage of the yarn end through a reference position are detected by a tension detector, each spindle has only to be provided with a tension detector at its reference position. Accordingly the present invention can be implemented by a very simple configuration with a minimum area of contact with the yarn in the yarn processing region.

As already mentioned, however, a device of the present invention must detect not only occurrence of a yarn breakage but also passage of the broken yarn end based on the tension signal from a tension detector. In view of this point, it is preferable to use a contact type tension detector that detects the tension of a running yarn by keeping a tension detection guide in contact with the yarn. More preferably, the tension detector should be able to reliably retain contact with the running yarn until the passage of the yarn end, and should have a smaller area of contact with the yarn in view of frictional damage and other effects on the yarn.

Such a tension detector is a cantilever tension detector having one contact point, combined with a tension detection guide having a ring- or U-shaped yarn guide to secure the contact with the running yarn. It is also possible to directly apply a well-known commercially available guide detection type tension detector in which a yarn guide and a tension detection guide are placed along the course of the running yarn and the tension of the yarn is detected based on the reactive force from the yarn or on the tension detection guide's displacement or distortion. This is a preferable application because placing the yarn guide and the tension detection guide along the yarn course allows reliable retention of the yarn until the yarn end passes the reference point.

Further, it is preferable that a tension detector of the present invention is provided with an elastic member, such as a spring, to support the tension detection guide, and its displacement is detected.

This is because the elastic system of the tension detection guide has a natural oscillation waveform and its beginning of appearance in the tension signal can be used to detect the passage of the broken end through a reference position (practically the position of the tension detection guide). This enables reliable detection of the time of passage of the yarn end.

There may also be other yarn breakage position detecting means dedicated for specific processing members and they may be useful if they can properly detect the position of a yarn breakage. However, it is preferable, in view of flexibility and cost, to use the arithmetic approach of the present invention that determines a yarn breakage position, as a yarn length from a reference position to the yarn breakage position, by arithmetically multiplying the speed of the running yarn by the period of time between occurrence of the yarn breakage and passage of the broken yarn end through the reference position.

For accurate detection of a yarn breakage position, it is more preferable to correct the above mentioned yarn length by taking into consideration the elongation of the yarn length by the tension effective before the yarn breakage, and use the corrected yarn length as the yarn breakage position relative to the reference position. If the production stage doesn't need more than identifying which processing member causes a yarn breakage, however, such highly accurate detection is not required and therefore this correcting system can be omitted.

BEST MODE FOR CARRYING OUT THE INVENTION

Figure 1:
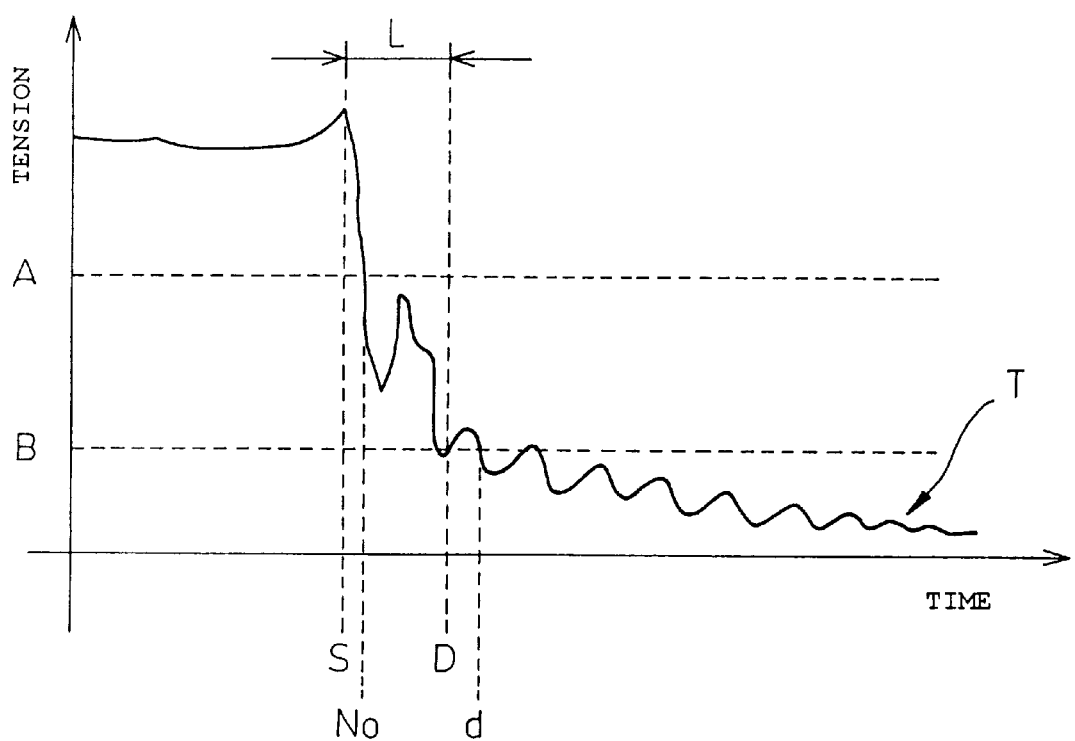
FIG. 1 is a graph indicating a change in an output signal of a tension detector with time when a yarn breakage occurs, in the embodiment of the present invention.
Figure 2:
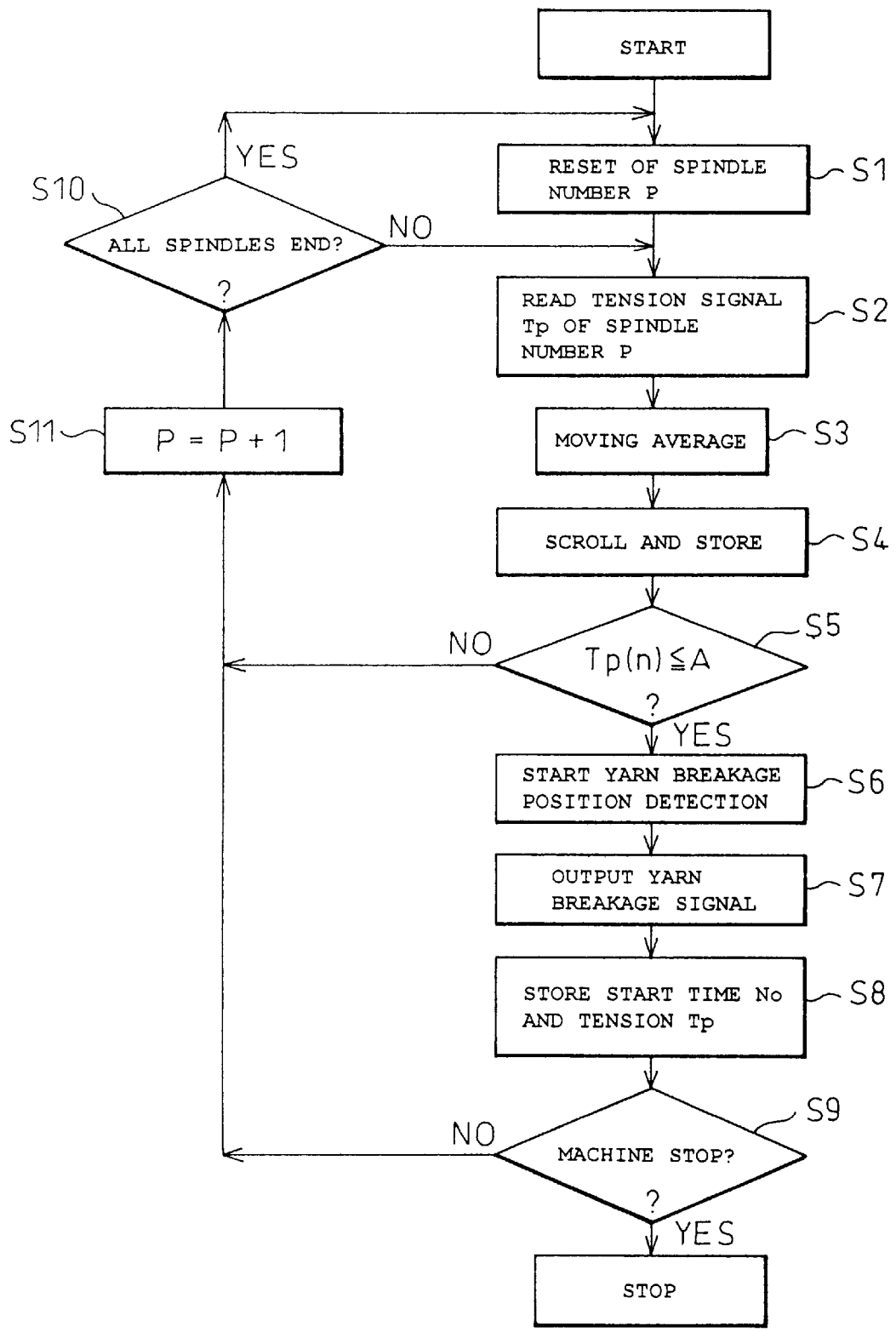
FIG. 2 is a flowchart of the basic processing means in the embodiment of the present invention.
Figure 3:
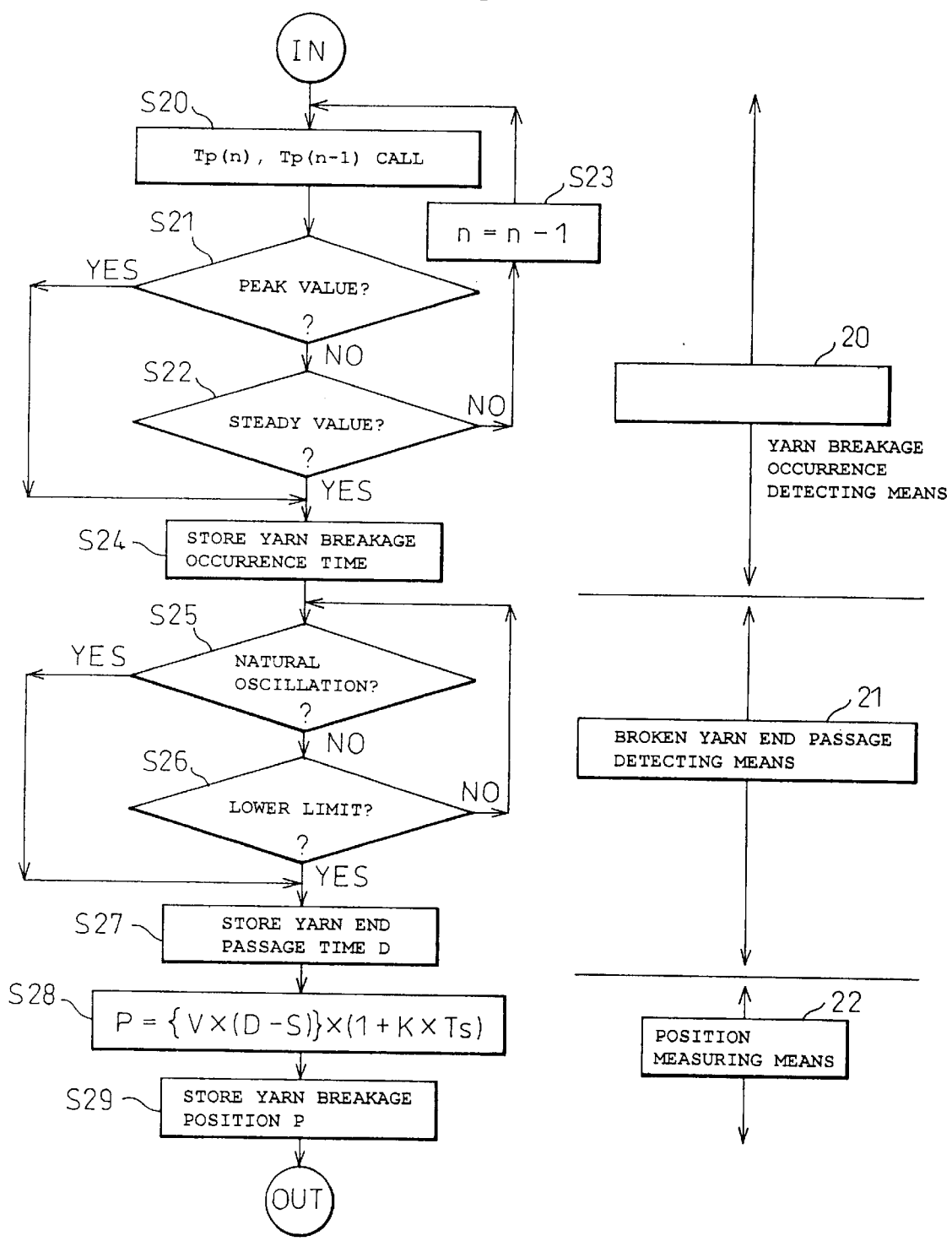
FIG. 3 is a flowchart of yarn breakage position detection in the embodiment of the present invention.
Figure 4:
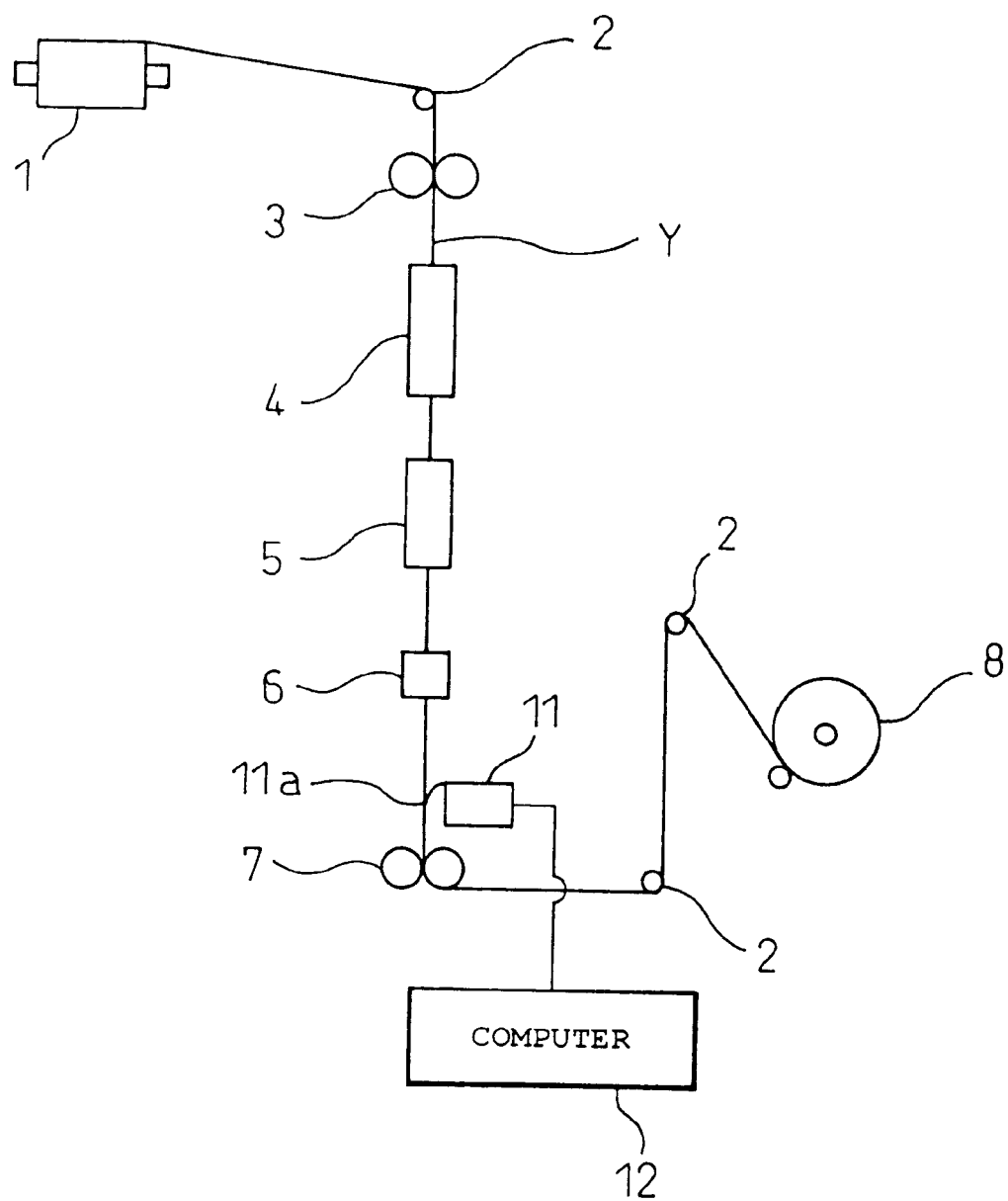
FIG. 4 is a view illustrates a false twister as an embodiment of the present invention.

The present invention will now be described in detail by way of a preferred embodiment applied to a false-twister with reference to the drawings. FIG. 1 is a graph indicating a change in an output signal of a tension detector with time when a yarn breakage occurs, in the embodiment. FIG. 2 is a flowchart indicating a scanning means of the tension detector of the embodiment. FIG. 3 is a flowchart indicating the process of yarn breakage position measurement in the embodiment. FIG. 4 shows the configuration of the false-twister to which the embodiment is applied. Needless to say, the application of the present invention is not limited to the stage of false twisting stage, but the present invention may also be applied to other production stages such as a spinning stage and a heating drawing stage, although detailed description are omitted here.

The false twister exemplarily shown in FIG. 4 is known from JP198712327, etc. In the false twister a yarn Y, fed from a supply package 1, goes through a guide roller 2 and is fed to a yarn processing region from feed rollers 3. Then, the yarn Y, fed to the yarn processing region provided over a certain length, is processed and treated by processing members such as a heater 4, a cooler 5, a frictional false twisting tool 6 providing both twisting and feeding actions, delivery rollers 7 and so on.

That is, in the yarn processing region, the yarn Y is false-twisted by the frictional false twisting tool 6 while being drawn at a drawing ratio determined by the feeding speed ratio of the delivery rollers 7 to the feed rollers 3. The false twist is thermally set in the false-twisted shape by the heater 4 and the cooler 5, and the yarn Y is thus subjected to a predetermined false-twisting process. Note that in the section downstream from the frictional false twisting tool 6, the false-twisted yarn Y is untwisted, and then, the yarn Y fed to the delivery rollers 7 is turned by two guide rollers 2, and formed to a processed yarn package 8 by a not shown winder. Also, here, with a yarn breakage managing device including a computer 12 is also provided.

The false twister includes a tension detector 11 for measuring the tension of the yarn in the yarn processing region, which is a basic element of a yarn breakage position detecting device of the present invention. The tension detector is placed between the frictional false twisting tool 6 and the delivery rollers 7 in the most downstream section of the yarn processing region, and connected to the computer 12. Any type of tension detector can be used suitably as the tension detector 11 as long as it can be in contact with the running yarn to measure the tension of the yarn.

Also, in the example, a commercially available detector is used which has a tension detection guide 11a supported by a cantilever elastic member so that influence exerted to the yarn Y due to tension measurement is small and the tension of the yarn Y is measured by detecting the deformation of the elastic member forced by the yarn Y. The tension detection guide 11a has a guide groove formed at a contacting portion with the yarn Y so that the contact between the tension detecting guide 11 and the running yarn Y is surely kept until the yarn end passes even if a yarn breakage occurs. A preferable material of a part of the tension detection guide 11a kept in contact with the yarn is a ceramic such as $Al_2O_3$, $Ti_2O_3$, or a metal base with a protective layer coated thereon such as hard chromium plating, because the guide surface made of such a material is less damaged or worn due to contact with the yarn. In addition, three-guide type tension detectors which have two more guides placed before and after the tension detection guide so that the yarn course is fixed, or two guide type tension detector in which one of said two guides is omitted, are applicable.

Now, FIG. 1 shows a graph of the tension signal T, which is a result of actually measuring a change in the tension of the yarn with time by the tension detector 11 when a yarn breakage occurs. In FIG. 1, the reference symbol S indicates the time when a yarn breakage occurs, and the reference symbol D indicates the time when the end of the broken yarn formed by the yarn breakage passes through the tension detection guide 11a.

The tension signal T from the tension detector 11 indicates a fluctuating pattern, such that the tension rises from the normal running state value to a peak at time S, then sharply drops, then rises again somewhat, and drops, as shown. After time D when the yarn end passes through the tension detector 11, however, the tension signal T gradually drops to the zero level with a continuously and gradually damping periodic signal. It is known that the detected periodic signal attributes to the natural oscillation of the tension detection guide system.

Here, the change in the tension signal T after occurrence of a yarn breakage shows as a whole a change with time which can be approximated by a first-order lag system, when viewing FIG. 1 as a large fluctuating waveform by removing influence of minor fluctuations due to the above mentioned periodic oscillation, etc. The reference symbol A refers to a predetermined yarn breakage decision value used to judge whether a yarn breakage has occurred, as described later. The reference symbol B is a lower limit value used to detect passage of a broken yarn end. A and B have the relation A>B.

The present invention has been accomplished by analyzing the tensional behavior of a broken yarn as described above, and is configured with the tension detector 11, a yarn breakage occurrence detecting means 20, a broken yarn end passage detecting means 21 and a yarn breakage position detecting means 22 so as to perform various processings, as shown in FIG. 3. Note that in this embodiment, a basic processing means is provided to read the tension signal from the tension detector after filtering high-frequency noise through a low-pass filter (LPF), to perform such processings as noise rejection and store the result. This basic processing means is accommodated in the device containing the computer 12.

As shown in FIG. 2, here, the basic processing means has a data collection functioning part sequentially scanning the tension detectors 11 of respective spindles to collect tension data of respective spindles, and a yarn breakage treatment functioning part judging occurrence of a yarn breakage to start necessary yarn breakage processes. In more detail, in the data collection functioning part, the spindle number P is reset (S1), the tension signal Tp is read from the tension detectors 11 of the spindles P (S2), a moving average (S3) is calculated, and the result is stored (S4), as shown in FIG. 2. As for the storage, a scroll type storing system is employed in the embodiment to save the capacity of memory, in which update data of a certain number obtained by the sampling within a certain time period necessary to detect a yarn breakage position are sequentially stored. As for the moving average calculation, three successive sampling data are averaged in the embodiment.

Next, in the yarn breakage treatment functioning part, an occurrence of a yarn breakage is judged (S5). If there is no occurrence of yarn breakage, the spindle number P for which an occurrence of a yarn breakage is judged is incremented by 1 (S11), and if the spindle number is not the last one (S10), the above mentioned data collection for the next spindle is conducted. In this way, an occurrence of a yarn breakage is judged for all the spindles. Then, if the check for an occurrence of a yarn breakage for all the spindles is completed, the spindle number P is reset (S1) to perform data collection from the spindle number 1.

Further, in S5 of the yarn breakage treatment functioning part, a calculated moving average of the tension signal Tp(n) is compared with the predetermined yarn breakage decision value A to judge whether a yarn breakage occurs or not. If no yarn breakage occurs (the result of S5 is NO, that is, the tension signal is not lower than the yarn breakage decision value A), the program directly returns to the data collection functioning part to collect tension data from spindles, as described above. If a yarn breakage occurs, a yarn breakage treatment routine is executed, as described below. That is, if the result of S5 is YES (that is, the moving average of the tension signal is lower than the yarn breakage decision value A), it is judged that a yarn breakage occurred (S6). In this case, the yarn breakage managing unit issues a yarn breakage signal which causes a yarn breakage treating member such as a yarn feed cutter to be started to operate (S7). In addition, after storing the data such as a judging time No and the tension value Tp (No) at that time necessary in the yarn breakage position detection, or maintenance and management, etc. (S8), described below, it activates a yarn breakage position detecting routine. Then, the program returns to the data collection functioning part to collect tension data of the next spindle (S9).

In the thus activated yarn breakage position detecting routine, a yarn breakage occurrence detecting means, which detects a yarn breakage, first proceeds to a yarn breakage occurrence detecting routine, as shown in FIG. 3. This yarn breakage occurrence detecting routine detects a yarn breakage time, based on the tension signal Tp(n) stored by the scroll method for the spindle P of concern, and retroacting that value from the judging time (No) of the yarn breakage occurrence as follows. In the embodiment, a normal value detecting method is primarily used and is combined with a peak value detecting method unique to the example in which a peak value is detected upon a yarn breakage and thus the present invention adopts a double detecting approach employing two methods having different detection priciples to provide an improvement in accuracy and reliability.

Practically, two successive retroactive values Tp(n−1) and Tp(n) (initial value of n is No in this case) are called and the program goes to a peak judgement step to judge whether there is a peak value or not (S21). This judgement is carried out in the preferred embodiment by comparing the value Tp(n) measured at the time n, which is one of values taken successively and retroactively from the time No at which occurrence of a yarn breakage is judged, with the Tp(n−1) measured at the time (n−1), which is preceding by one. "The time of the peak value" is determined at the time when the relationship, Tp (n)≧Tp(n−1) is satisfied. If the judgment of S21 is YES (that is, the above relationship is satisfied), the program goes to a step for storing a yarn breakage occurrence time S and the time n at which the relationship is satisfied is stored as the yarn breakage occurrence time S (S24).

On the other hand, if the judgement of S21 is NO (that is, no peak value is detected), the program goes to a steady state decision step in which it is judged whether it is a steady state or not (S22). In this embodiment, this judgement is carried out by judging whether |Tp(n)−Tp(n−1)|≦α (α is a predetermined value) continues for a predetermined time period m. If the judgment of S22 is NO, n is retroacted to (n−1) (S23), to call Tp(n−1) and Tp(n<2) before Tp(n−1), and the peak decision step and steady state decision step are performed again, and this is repeated until a steady state is found.

If the judgement of S22 is YES, that is, the tension signal is judged as being in steady state, the program goes to the yarn breakage occurrence time storage step (S24), to store the yarn breakage occurrence time S, in which the yarn breakage occurrence time S is stored as a time at which a difference less than the predetermined value α begins to continue in the retroactive analysis, in particular, a time after the predetermined continuous period m from the time n at which judgement of S22 becomes YES (n+m). In other words, this judgement detects a time at which the tension signal shows a drop larger than the predetermined magnitude a from the previous measurement.

As described, the peak decision step in the embodiment detects the peak point in FIG. 1 as the yarn breakage occurrence time so as to make the detection as accurate as possible. If such a peak is not observed, the steady state decision step finds a time when the tension dropped more than a certain amount α from the steady state tension of the normally running yarn and considers the time as the yarn breakage occurrence time. This secures unfailing and reliable detection. The yarn breakage occurrence time S is detected and stored in this manner. Accordingly, the yarn breakage occurrence time S can be detected accurately as shown in an example measurement of FIG. 1. Note that using only the latter method (steady state decision method) is enough to identify which part has caused a yarn breakage. In some cases, it is also not a problem to use only the former method (peak decision method).

This yarn breakage occurrence time detection can also be implemented by electronic circuitry such as a comparator. Because the required yarn breakage treatment process is done by a scanning means, however, this detection process must not be so fast and therefore software processing using a computer, as in the example embodiment, is advantageous in view of flexibility, operability, etc. In addition, software processing is not limited to the two detecting methods in the example embodiment. Because a yarn breakage causes a large drop of tension as observed in the example measurement, detection is also possible by such a method as sequentially examining the differentiated tension signal drop or the non-differentiated signal drop per period (generally the scanning period) and, if the drop exceeds a predetermined amount in a period, it is judge that a yarn breakage occurred in that period.

After detection of the yarn breakage occurrence time is completed by the yarn breakage occurrence detecting means, the program goes to a yarn end passage detecting routine by a yarn end passage detecting means to detect the time when the yarn end passed through the reference position. For this detection, a double detecting approach is employed, in the embodiment, to increase the reliability of detection by using a natural oscillation detecting method and a lower limit detecting method having different detecting priciple. That is, in the tension detector 11 in which the yarn Y contacts the tension detection guide 11a, a natural oscillation detecting method primarily uses the natural oscillation, inherent to a tension detecting guide system shown in FIG. 1, which appears after the end of the yarn passes. In this case, if natural oscillation is not found, the yarn end passage time can be obtained by detecting a time at which the tension becomes lower than the predetermined lower limit B, which is predetermined for the detection of the yarn end passage.

Accordingly, the yarn end passage detecting process in the embodiment comprises a natural oscillation judging step to detect the beginning of the natural oscillation (S25) and a lower limit judging step (S26). Here, in the natural oscillation judging step (S25), a tension signal $Tp(n)$ obtained at a time after an experimentally predetermined time period from the yarn breakage judgement and the subsequent signal $Tp(n+1)$ are called, and it is judged whether $Tp(n) \leq Tp(n+1)$ is satisfied or not (substep 1). If the relationship is satisfied, $Tp(n)$ is stored as a local minimum value "min" together with the satisfied time n, and the minimum value flag is set. If the relationship is not satisfied, judgement of the substep 1 is NO, and the program goes to the next lower limit judging step (26).

Once the minimum flag is set, in the substep 2 of the natural oscillation judging step (S25) it is judged whether $Tp(n+1) \geq Tp(n+2)$ is satisfied or not, and if the relationship is satisfied, $Tp(n+1)$ is detected as a maximum value "max" following the minimum value "min". If the relationship is not satisfied, judgment of the substep 2 is NO, and the program goes to the following lower limit judging step (S26) as in the case of the minimum value.

If the relationship of the substep 2 is satisfied, the program goes to the step (S27) in which it is judged whether the difference (max−min) is smaller than an amount predetermined based on actual tests and, if so, stores n (time when the minimum value was measured) as the yarn end passage time D. If the difference is larger than the predetermined amount, it is judged that there is no natural oscillation, the minimum value flag is reset. In this case, due to the judgement of NO by the natural oscillation judging step (S26), the program goes to the following lower limit judging step (S26). As can be understood from FIG. 1, the natural oscillation detecting method provides accurate detection in the example embodiment.

If judgment of the natural oscillation judging step (S25) is NO, the program goes to the lower limit judging step (S26) as shown. This step judges whether the tension signal $Tp(n)$ is continuously lower than a certain level predetermined relative to the steady state level of the running yarn (practically 25% in the embodiment) during a predetermined period. If the result is NO, time n is incremented to (n+1) and the natural oscillation judging step is repeated.

On the other hand, if judgement of the step 26 is YES, that is, the tension signal is continuously lower than the lower limit, the program goes to the following step (S27) to store the broken end passage time D. In this case, time n when the tension signal became lower than the predetermined level is stored as the broken end passage time D. This lower limit detecting method improves the reliability of yarn end passage detection because the characteristic vibration may not be always clear. In the embodiment of FIG. 1, the yarn end passage time D is detected by the natural oscillation method, while d is a corresponding time detected by the lower limit detecting method.

To detect passage of a yarn end, both methods should be used as shown by the embodiment but, in some cases, using only one of the two methods is not a problem. In short, one or more suitable detecting methods should be used either for either yarn breakage occurrence detection or yarn end passage detection based on the result of preliminary experiments to check the behavior of the output signal from the extension detector when a yarn breakage occurs.

As described hereinabove, after the necessary processing is done by the yarn end passage detecting means, the position measuring means is started to perform a position measuring process and the yarn breakage position is measured. That is, a time period L during which the yarn end travels from the yarn breakage occurrence position to the reference position can be obtained from the time difference, from the yarn breakage occurrence time S and the yarn end passage time D. Also, the travel speed V of the yarn end (namely the yarn Y) is known as a predetermined value from the winding speed yarn Y. Therefore, the distance from the reference position to the yarn breakage occurrence position can be measured by the product L×V.

That is, a yarn breakage position can be located by detecting the time when the yarn breakage occurs in a certain area such as a yarn processing region, then detecting the time when the end of the yarn passes through a reference position downstream from that area, and using the period from the yarn breakage occurrence time to the yarn end passage time.

By the way, just before a yarn breakage occurs, the yarn Y is running with a constant tension, given normal operation, and for accuracy, correction is preferable in consideration of this tension. Therefore, in the embodiment, as shown in calculation step (S28) in FIG. 3, based on the difference between the times, and from the predetermined running speed V of the yarn Y, and the steady state tension Ts of the yarn Y running at V, the yarn length from the reference position, i.e., the yarn breakage position P is calculated according to the following equation (1) below. The yarn breakage position P calculated in this manner is stored together with the yarn breakage occurrence time S and the yarn end passage time D after converted into a convenient format for later use (S29).

$$P=\{V\times(D-S)\}\times(1+K\times Ts) \qquad (1)$$

Where, K is the elastic modulus of the yarn Y.

By using the yarn breakage position data obtained in this manner, it is possible to determine the position in the yarn processing region at which a yarn breakage is caused. This makes it simpler and quicker to clarify the causes of yarn breakage in each spindle and therefore to achieve the desired object of the present invention.

While the present invention has been described with respect to a specific embodiment, it is clear from the purport of the present invention that the present invention is not limited to that embodiment.

INDUSTRIAL APPLICABILITY

With a simple configuration where means such as a tension detector is used for tensional measurement at a reference position in each spindle, as described above, the present invention provides not only a currently available capability of detecting occurrence of a yarn breakage but also an online capability of knowing where the yarn breakage occurs. The yarn breakage position detection is directly connected to each stage of production while an effect on the quality of the yarn is minimized. The invention provides great help in the online analysis of the causes of yarn breakage in a large textile manufacture plant. Further, by enabling prompt countermeasures to yarn breakage, it will bring about earlier stabilization of a plant and therefore contribute greatly to improvements both in productivity and yarn quality.

What is claimed is:

1. A method of detecting a yarn breakage position where a running yarn is broken in a yarn processing facility, comprising the steps of:
    detecting occurrence of yarn breakage by monitoring tension of the running yarn;
    detecting passage of an end of the broken yarn through a reference position;
    detecting a period of time from occurrence of the yarn breakage to passage of the broken yarn end; and
    calculating the yarn breakage position based on the detected period of time and said reference position.

2. The method of detecting a yarn breakage position, according to claim 1, wherein the step of detecting the passage of the broken yarn end through the reference position is carried out by monitoring the tension of the running yarn.

3. The method of detecting a yarn breakage position, according to claim 1, wherein the step of detecting the occurrence of a yarn breakage and the step of detecting the passage of the broken yarn end through the reference position are carried out by monitoring the tension of the running yarn by a common tension detector.

4. The method of detecting a yarn breakage position, according to claim 3, further comprising the steps of:
    detecting and storing a first time when the occurrence of the yarn breakage is detected;
    detecting and storing a second time when the passage of the broken yarn end through the reference position is detected; and
    measuring a period of time from the occurrence of the yarn breakage to the passage of the broken yarn end through the reference position based on said first time and said second time.

5. The method of detecting a yarn breakage position, according to claim 4, comprising the steps of:
    sampling and storing the tension of the running yarn at the reference position, at constant sampling intervals, as a tension signal; and
    determining said first time as at least one of a time when the tension signal becomes a peak value before a yarn breakage judgement time at which it is judged that a yarn breakage occurs and a time when the tension signal begins to decrease from a steady state level obtained during normal operation before the yarn breakage judgement time.

6. The method of detecting a yarn breakage position, according to claim 5, wherein said yarn breakage judgement time is determined as the earlier one of the time when the tension signal becomes a peak and the time when the tension signal begins to decrease from the steady state level.

7. The method of detecting a yarn breakage position, according to claim 5, wherein it is judged that a yarn breakage occurs when the detected tension of the running yarn become lower than a first value, and said second time is determined as at least one of a time when said tension signal becomes lower than a second value lower than said first value after the judgement of the occurrence of a yarn breakage is made and a time when said tension signal begins to show natural oscillation.

8. The method of detecting a yarn breakage position, according to claim 7, wherein said second time is determined as earlier one of a time when said tension signal becomes lower than a predetermined level and a time when said tension signal begins to show a natural oscillation.

9. The method of detecting a yarn breakage position, according to claim 1, wherein the yarn breakage occurrence position relative to the reference position is calculated based on a yarn length obtained by multiplying the running speed of the yarn by the time period from occurrence of the yarn breakage to the passage of the yarn end.

10. The method of detecting a yarn breakage position, according to claim 9, wherein, upon calculation of the yarn length, a real yarn length is calculated by performing correction in consideration of the elongation due to the tension before the breakage and the yarn breakage position relative to the reference position is calculated using the real length during running.

11. A device of detecting a yarn breakage position to detect a position where a running yarn is broken in a yarn processing facility, comprising:
    a tension detector arranged at a reference position and made in contact with the running yarn to detect tension of the running yarn;
    a yarn breakage occurrence detecting means detecting a first time when a breakage of a running yarn occurs from a tension signal of the tension detector;
    a yarn end passage detecting means detecting a second time when an end of the broken yarn passes through the reference position from the tension signal of the tension detector; and a yarn breakage position detecting means detecting the yarn breakage position relative to the reference position based on said first time and said second time.

12. The device of detecting a yarn breakage position, according to claim 11, wherein said yarn breakage occurrence detecting means detects a third time when the tension signal becomes lower than a first value, and said first time is determined as one of a time when the tension signal shows a peak level before the detection of said third time, and a time when the tension signal begins to decrease from the steady state level.

13. The device of detecting a yarn breakage position, according to claim 12, wherein said yarn end passage detecting means determines said second time as one of a time when the tension signal becomes lower than a second value lower than the first, and a time when the tension signal begins natural oscillation.

14. The device of detecting a yarn breakage position, according to claim 11, wherein said yarn breakage position detecting means calculates the yarn breakage occurrence position relative to the reference position based on a yarn length obtained by multiplying the running speed of the yarn by the time period from the occurrence of the yarn breakage to the passage of the yarn end.

15. The device of detecting a yarn breakage position, according to claim 14, wherein said yarn breakage position detecting means is a means which calculates the real yarn length by performing correction in consideration of the elongation due to the tension before the breakage, and the yarn breakage position relative to the reference position using the real length during normal operation.

* * * * *